(12) United States Patent
D'Amore et al.

(10) Patent No.: US 7,931,879 B2
(45) Date of Patent: Apr. 26, 2011

(54) CONTAINERS AND METHODS FOR THE AUTOMATED HANDLING OF A LIQUID

(75) Inventors: Alessandro D'Amore, Wohlen (CH); Siegfried Mueller, Meierskappel (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 1329 days.

(21) Appl. No.: 11/481,745

(22) Filed: Jul. 5, 2006

(65) Prior Publication Data

US 2007/0017927 A1 Jan. 25, 2007

(30) Foreign Application Priority Data

Jul. 7, 2005 (EP) ..................................... 05106198

(51) Int. Cl.
*B01L 3/00* (2006.01)
(52) U.S. Cl. ....... 422/550; 422/942; 422/948; 220/23.8; 220/263; 220/315; 220/324
(58) Field of Classification Search .................... 422/99, 422/102, 916, 939, 940, 941, 942, 550, 569; 220/23.2, 23.8, 203.09, 203.1, 263, 315, 220/324, 577, 669, 675
See application file for complete search history.

(56) References Cited

U.S. PATENT DOCUMENTS

| | | | | |
|---|---|---|---|---|
| 3,415,361 A * | 12/1968 | Chambliss et al. | ........... | 206/221 |
| 4,769,335 A * | 9/1988 | Schmidt et al. | ............... | 436/176 |
| 5,005,721 A * | 4/1991 | Jordan | ......................... | 220/23.4 |
| 5,145,646 A * | 9/1992 | Tyranski | ....................... | 422/102 |
| 5,382,408 A | 1/1995 | Perlman | ....................... | 422/102 |
| 5,577,626 A | 11/1996 | Henkel et al. | .................. | 215/237 |
| 5,578,494 A | 11/1996 | Clark et al. | ..................... | 436/54 |
| 5,720,406 A | 2/1998 | Fassbind et al. | | |
| 7,138,091 B2 * | 11/2006 | Lee et al. | ..................... | 422/102 |
| 2003/0102323 A1 | 6/2003 | Lohn | | |
| 2004/0018122 A1 | 1/2004 | Micklash et al. | ............. | 422/130 |

FOREIGN PATENT DOCUMENTS

| | | |
|---|---|---|
| CA | 2083201 A1 | 5/1993 |
| DE | 10333197 A1 | 2/2005 |
| EP | 0 642 828 B1 | 3/1995 |
| EP | 1 450 161 A8 | 8/2004 |
| EP | 05106198.4 | 12/2005 |
| EP | 05106198.4 | 2/2006 |
| JP | 60-52281 | 3/1985 |
| JP | 64-61667 | 3/1989 |
| JP | 2-275362 | 11/1990 |
| JP | 03226485 | 10/1991 |
| JP | 2005-61897 | 3/2005 |
| WO | WO 95-08774 A2 | 3/1995 |
| WO | WO 95-08774 A3 | 3/1995 |
| WO | WO 2004/054715 A1 | 7/2004 |

* cited by examiner

*Primary Examiner* — Jill Warden
(74) *Attorney, Agent, or Firm* — Olga Kay; David J. Chang (57) ABSTRACT

The invention relates to a method for the automated handling of a fluid biological sample in an analytical instrument. Furthermore, the invention provides containers as well as instruments and systems suitable for the automated handling and processing of the fluid biological sample and discloses production methods for the manufacture of the containers.

14 Claims, 6 Drawing Sheets

CONTAINERS AND METHODS FOR THE AUTOMATED HANDLING OF A LIQUID

BACKGROUND OF THE INVENTION

1. Field of the Invention

This application claims the benefit of priority under 35 U.S.C. §119 of EP Application 05106198.4, filed Jul. 7, 2005, the contents of which are hereby incorporated by reference.

The invention relates to a method for the automated handling of a fluid biological sample in an analytical instrument in the field of nucleic acid purification and amplification.

The invention further relates to a container and a tube suitable for the use in an analytical instrument, wherein a fluid biological sample is handled automatically as well as the instrument capable of handling and processing the fluid biological sample.

Moreover, the invention relates to a system capable of analyzing a biological sample by utilizing an instrument for the automated handling of a liquid in combination with a container in which the biological sample is processed.

Additionally, the invention relates to a method for the production of a container consisting of three plastic materials using the so-called multi component injection molding technology which allows the manufacturing of a product with different materials in one mold.

2. Description of the Related Art

The polymerase chain reaction (PCR) is an important and widespread method for amplification and analysis of nucleic acids. For performing PCR reactions reaction vessels have to fulfill a number of requirements. Vessels have to be tightly dosed during PCR reaction to avoid evaporation of liquid from the vessel. Furthermore, the temperature of the liquid inside the vessel has to promptly follow the outside default temperature given by a heating and/or cooling installation stipulating certain thermal conduction properties upon the vessel material. In specific PCR applications optical measurements are carried out during the course of the amplification leading to particular optical requisites of the vessel material regarding transparency and auto-fluorescence.

For PCR applications a variety of embodiments for vessels are common. Whereas most of them exhibit a similar shape, namely, a tube comprising a reversibly closable opening on the one end and a conically tapered permanently dosed second end, several embodiments regarding the closure, the spacial alignment and/or the combination of tubes are known. Thus, closures may be firmly attached to the tube or may be provided by a separate cap portion. Furthermore, besides their use as single vessels particular vessels may be combined and arranged to form plates comprising 96 or 384 cavities or strips comprising 6 or 8 tubes.

Such an arrangement of reaction vessels is described in EP 0642828, wherein a first part comprising reaction vessels of identical shape and dimension set up annularly and a second part comprising closures suitable for closing the reaction vessels gas-tightly also arranged annularly form a disposable arrangement of reaction vessels for carrying out temperature cycling of a liquid mixture. While these closures are placed into the openings to tightly seal the tube,
EP 0907083 displays a sample cup, which can be closed by a removable and screwable cap. Another vessel systems for treating and/or storing liquids is disclosed in US 20040234422 comprising a two-dimensional vessel arrangement with a plurality of vessels which are open at the top and which are interconnected to form a unit, and a two-dimensional closure arrangement which has an arrangement of closure elements corresponding to the vessel arrangement and by means of which the openings of the vessels can be closed.

Disposable polypropylene tubes for performing PCR typically have a lower conical portion and an upper cylindrical portion, wherein the lower portion contacts a correspondingly shaped hole in a heating block and has a substantially thinner wall than that of the upper portion of the tube. EP 1275438 discloses that the wall thickness of the conical section is in the range from 0.009 to 0.012 inches (0.2286 to 0.3048 mm) plus or minus 0.001 inches (0.0254 mm) with 0.012 inches (0.3048 mm) being the mostly preferred embodiment, while the wall angle relative to the longitudinal axis of the tube is typically 17° in the lower conical portion.

U.S. Pat. No. 5,382,408 discloses a micro-centrifuge tube having a container having a round opening and a frictionally seated lid being dimensioned to corer the opening and hingedly connected to the container. The lid has a lid extension extending upwardly from the lid surface and outwardly away from the hinge in such a manner which allows the lid to be unseated and moved from the opening of the container. Said frictionally seated lid has the disadvantage that the retention force of the lid on the tube is mainly depending on the diameter of the annular lid seal (on the underside of the lid) respectively on the diameter of the round opening of the micro-centrifuge tube and tends to vary, which is typical for injection molded parts. This might become even a major disadvantage when an internal pressure in the tube causes a force against the lid.

U.S. Pat. No. 5,577,626 disclose a closure having a base for attachment to a container at the opening and a lid hingedly connected to the base. The lid has an outwardly projecting engaging member whereby the user can release the latch and apply a force to the engaging member to lift the lid via the member. However, such closures are not useful for automated opening the lid as it requires two simultaneous movements: release of the latch and at the same time lift the lid via member. After a first little move of the lid, the object releasing the latch has to remove, which represents a further inconvenience for automated opening.

As automatic preparation and processing of biological samples is advantageous in many cases and becomes increasingly important, many PCR tubes available are adapted to the needs of fully automated procedures in robotic apparatuses. However, only few PCR vessels are capable of being fully automatically closable. EP 0907083 discloses such a vessel and an apparatus for automatically handling sample cups dosed with a screwable cap, wherein the apparatus is characterized in that it comprises a rotatable gripper tool apt to enter and engage with a recess of a vessel cap to form a connection which can be locked by rotating the gripper tool in a first sense and unlocked by rotating the gripper tool in a second sense opposite to the first. Besides, U.S. Pat. No. 5,578,494 describes a method for opening and closing a cap pivotally mounted on a container for storing reagents for the use in an automated analytical instrument by an actuating device.

All of these embodiments for the fully automated opening and closing of vessels have the common disadvantage, that there is one single closure for each single opening. Thus, in fully automated processes a multitude of single movements have to be performed leading to an increased complexity of the diagnostic process and thereby to decreased reliability. Moreover, with increasing complexity and increasing number of single movements the risk of spilling of liquid from the vessel drastically increases. Another disadvantage of these embodiments is speed and low operational capacity of automated processes as every single tube has to be opened successively. Furthermore, common PCR vessels applicable for fully automated closure either comprise screw tops or bayonet sockets demanding a robotic capable of rotary motions, which constructively is very complex and costly.

Furthermore, the problem of providing a sealing device to form a gas-tight seal for the efficient performance of analytical techniques such as the polymerase chain reaction has been addressed in U.S. Pat. No. 5,721,136 describing a multilayer composite sheet of material seals consisting of an elastically or inelastically deformable sealing layer having a tacky surface calendared or cast onto a relatively thin backing layer made up from any substance with low permeability to water vapor. This multilayer composite sheet may be placed over the openings of one or more reaction vessels in order to simultaneously seal one or more vessels for thermal cycling. Besides, EP 0836884 describes a seal for one or more vessels consisting of two elastic components, wherein a first seal provides an inner fluid-tight closure and a second outer closure provides a pressure seal to the vessels.

However, such embodiments have the disadvantage that the cover and/or seal is not permanently attached to the vessel and, therefore, may not be used for the automated handling of vessels comprising the repeated opening and closing of the cap portion without an increased probability of cross-contamination.

Thus, there is a need for providing methods and vessels for the fully automated handling of a liquid comprising more than one tube portion and a means for the handling including the repeated opening and closing of these tube portions in an easy and uncomplicated way.

SUMMARY OF THE INVENTION

A main object of the invention, therefore, is to provide methods, instrumentation, and vessels for the fully automated handling of a liquid comprising more than one tube portion and a means for closing these tube portions in an easy and straightforward manner at the same time without the need for a complex constructive and mechanical solution leading to low reliability and high costs. Furthermore, the format and properties of the vessels should be optimized for performing polymerase chain reactions within the analytical, instrument.

According to a first aspect of the invention, this problem is solved by a method for automated handling of a liquid in an analytical instrument comprising
    providing on the analytical instrument
        a container comprising
            a cup portion held in a receptacle and having an opening, and
            a cap portion comprising a cover closing the opening and being permanently attached to one side of the cup portion, and
        a handling head
    approaching the handling head to a side of the container having a closure by which the cover is vertically and reversibly fixed for closing the opening,
    horizontally asserting pressure by the handling head on the closure to release the cover from the vertical and reversible fixation, and optionally
    raising the cover by raising the handling head to open the cup portion.

According to a second aspect of the invention, the above aim is attained by using a container for the automated handling of a liquid on an analytical instrument comprising a cup portion having an upper opening, a cap portion permanently attached to one side of the cup portion comprising a cover closing the upper opening, and a closure comprising a latch-fit located at a side of the cup portion by which a snap-latch of the cap portion is held so that the cover is vertically and reversibly closing the opening, the snap-latch comprising a sloped plain accessible by a handling head from the side of the cup and releasing the cap portion from the cup portion by horizontally asserting pressure to the plain.

According to a third aspect of the invention, the above objective is achieved by using a tube for automated handling of a liquid on an analytical instrument comprising a cup portion having an upper opening consisting of a substantially conical first wall portion and a substantially cylindrical downwards tapered second wall portion, wherein the first wall portion has a substantially thinner wall than the second wall portion and wherein the angle defined by the longitudinal axis through the substantially conically shaped first wall portion is between 7° and 15°, more preferably between 8° and 12°, and most preferably between 9° and 11°.

According to a fourth aspect of the invention, the above goal is met by using an instrument for automated handling of a liquid comprising a handling head comprising a portion having a spike pointing in horizontal direction and a portion for vertically picking up items.

According to a fifth aspect of the invention, the above purpose is accomplished by a system for analysis of a liquid comprising an instrument according to the invention and a container according to the invention.

According to a sixth aspect of the invention, a vessel for achieving the above aim consisting of three plastic materials, is manufactured according to a production method using the so-called multi-component injection molding technology, which allows the manufacturing of a product with different materials in one mold.

According to a seventh aspect of the invention, the above problem is solved by using a vessel produced according to the production method described in the sixth aspect of the invention comprising a cup portion molded from a first rigid synthetic material, a cap portion cast from a second rigid synthetic material, and a seal portion cast from a soft synthetic material.

The main advantage of the invention is that the movements required for opening and closing of the container allow for a simplified automated process and therefore, a simplified construction of the robotic performing these tasks as no rotary motions have to be carried out leading to a decrease in complexity of the diagnostic process, an increase in reliability, and thus, to a decrease in costs.

A further advantage of the invention is the matter that the cap portion of several cup portions can be opened or dosed at the same time resulting in a reduced number of robotic movements also leading a decreased complexity and, thus, to an increased reliability and a higher operational capacity of the system for performing diagnostic processes.

An additional advantage of the invention is the permanent attachment of the cap portion to one side of the cup portion since no additional space within the system for performing fully automated diagnostic processes is required for the intermediate storage of the caps during the process is conducted. Furthermore, the erroneous closure of a cup portion with a cap is omitted.

A particular advantage of the production method is the permanent Junction of the different components without the use of complex and time-consuming assembling methods (e.g. welding).

BRIEF DESCRIPTION OF DRAWINGS

Embodiments of the invention are described below, by way of example, with reference to the accompanying drawings, wherein:

FIG. 7 A-D shows four cross sectional views through different embodiments of the invention with different cross sectional shapes of the sealing portion (14).

DETAILED DESCRIPTION OF THE INVENTION

As used herein, the term 'analytical instrument' refers to an instrument capable of the automated handling and processing of a liquid. In one embodiment, the analytical instrument may be used for the fully automated performance of nucleic acid purification and/or amplification. In this connection a 'handling head' is considered to be a part of the analytical instrument able to be moved and controlled by the control unit of the analytical instrument in a horizontal plane encompassing at least one gripper, which can be moved by the control unit in vertical direction. A 'gripper' is regarded as a tool to reversibly contain and hold a vessel or container, preferably having two movable parts comprising on one of the movable parts a spring mounted portion which is advantageous for the closing of a cap and on the other of the movable parts a step to allow the opening of the cap.

A container according to the invention is made up of a cup portion having an upper opening, a cap portion, which is permanently attached to one side of the cup portion, and a closure comprising a latch-fit located at the side of the cup portion by which the snap-latch of the cap portion is held so that the cover is vertically and reversibly closing the opening of the cup portion. The latch-fit and the snap-latch constitute a spring lock which is designed to fulfill a reversible lock of the cap portion onto the cup portion and thus acts as a reversible closure of the container.

Figure 1:
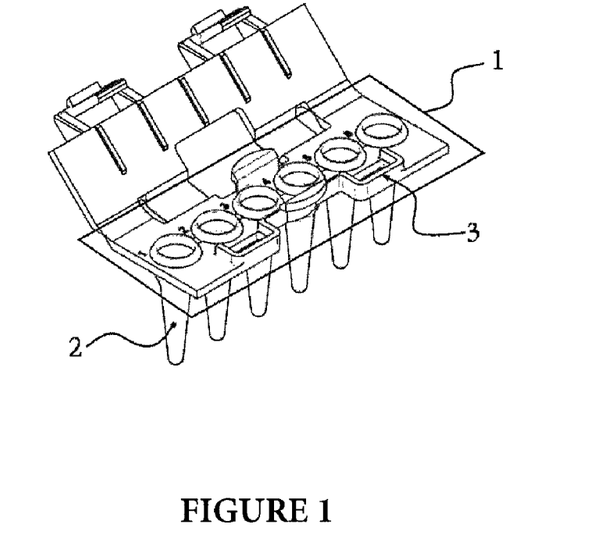
FIG. 1 is a view of a first embodiment of the invention in its open position with the highlighted cup portion (1) comprising tubes (2) and latch-fits (3).
Figure 2:
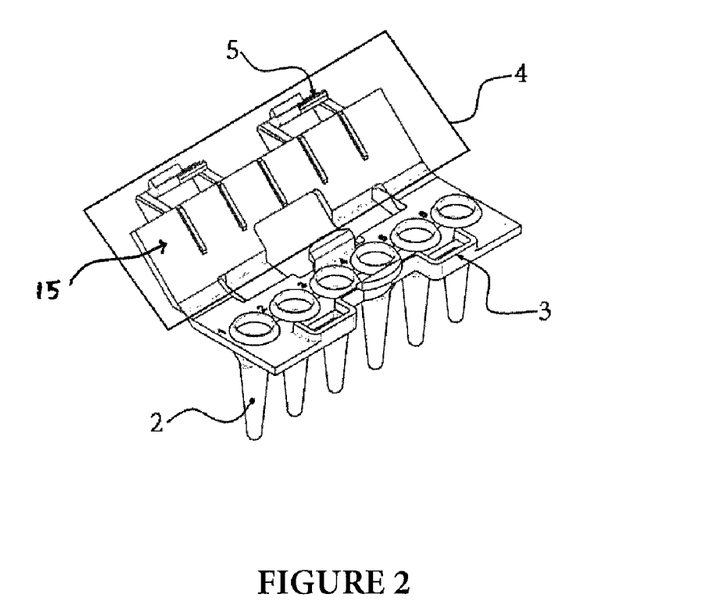
FIG. 2 is a view of a first embodiment of the invention in its open position with the highlighted cap portion (4) comprising snap-latches (5) and covers (15).

FIG. 1 shows a first embodiment of the container in its open position. The cup portion is highlighted (1) and contains a number of single tubes (2) in a specific arrangement, preferably in a linear arrangement, further comprising one or more latch-fits (3). The first embodiment of the container is also depicted in FIG. 2 highlighting the cap portion (4), which is permanently attached to one side of the above-mentioned cup portion and comprises a cover closing the upper openings of the cup portion. Furthermore, the cap portion exhibits one or more snap-latches (5) located in such a manner to reversibly engage into the latch-fits (3) of the cup portion, wherein the snap-latch (5) comprises a sloped plain accessible by a handling head from the side of the cup to allow releasing the cap portion from the cup portion when the handling head horizontally asserts pressure to the plain.

In certain embodiments the container consists of an alignment of 2 to 12 tubes each having an opening, wherein all openings can be closed and opened by the cover of the cap portion simultaneously and automatically.

Figure 3:
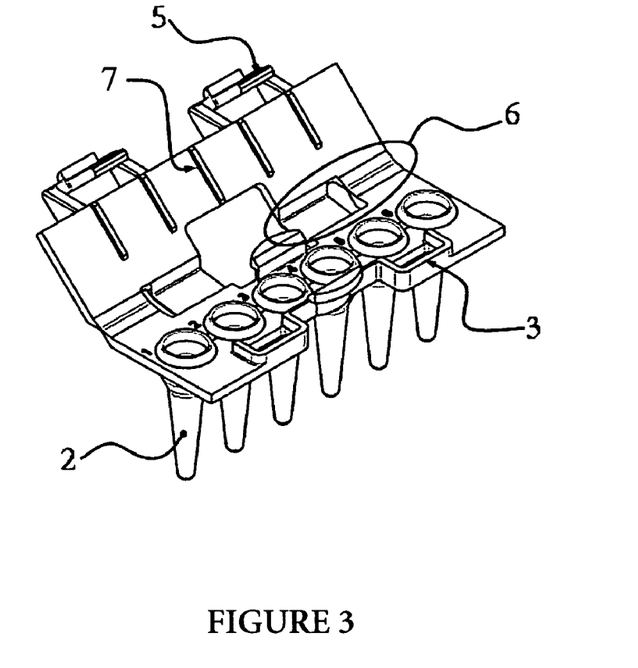
FIG. 3 is a view of a first embodiment of the invention in its open position consisting of six tubes (2). Cup portion and cap portion are connected via a bistable hinge (6). Partition bars (7) as well as the snap-latches (5) can be seen on the cap portion (4).

In a specific embodiment of the invention the cap portion of the container is permanently attached to one side of the cup portion via a bistable hinge (6). A bistable hinge is formed using a specific configuration of the hinge elements. Herein, the first hinge element simply consists of a thin wall connecting one side of the cup portion to one side of the cap portion representing the rotation axis of the cap movement. The second hinge element is formed as a thin wall with very thin connections to the cup portion and the cap portion, respectively and represents a spring capable of holding the cap in two different stable positions. Thus, the combination of these two hinge elements results in a bistable hinge. Such bistable hinges are well known to persons skilled in the art. The advantage of this embodiment is that the open and the closed position of the cap portion are preferred and stable positions. Hence, even if the container has been closed and stored in the closed position for a long period of time before being transferred and used on the instrument, the container remains in the open position for further processing after being opened using the handling head.

FIG. 3 shows another embodiment of the container, wherein the cover of the cap portion comprises at least one partition bar (7). The partition bar is located on the inner part of the cap portion and is positioned in such a way to separate one upper opening of a cup portion from a second adjacent upper opening when the cover of the cap portion is tightly fixed to the cup portion. Therefore, the partition bar acts as a barrier for fluid deposit on the inner side of the cap portion caused by evaporation during thermal cycling processes and can be regarded as an additional advantageous means for the avoidance of cross-contamination between the reactions mixtures in adjacent cup portions.

In a further embodiment of the invention the container comprises a cap portion that is non-transparent leading to the advantage of a reduction in auto-fluorescence and in light scattering as well as an improved recognition of the container when the container surpasses a light barrier.

Figure 4:
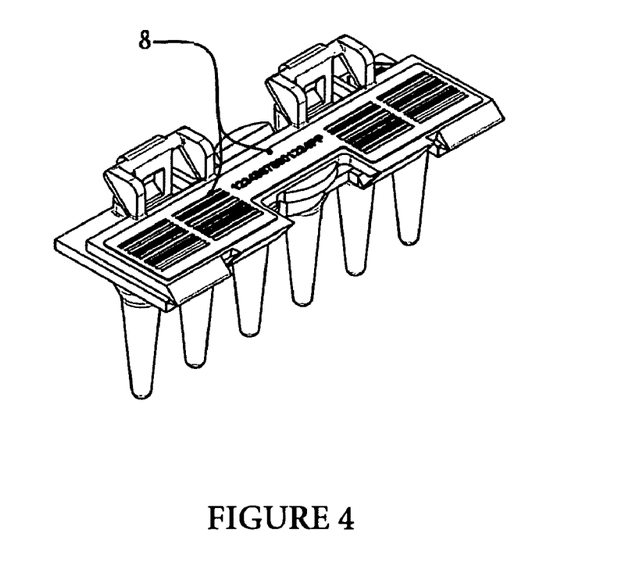
FIG. 4 is a view of a first embodiment of the invention in its closed position. On the upper side of the cap portion a barcode label (8) is attached.

A specific advantage of an embodiment of the container according to the invention, wherein the external part of the cap portion is formed as a planar surface is the possibility to mark this planar surface with a barcode (8) as depicted in FIG. 4 in order to allow for a definite identification of the container within the system while the fully automated diagnostic process is performed. In a further embodiment of the invention the barcode is divided into four parts with the top of the bars of each part facing towards the more narrow side rim and wherein the four parts of the barcode assemble one full length barcode. This embodiment is advantageous as it allows the insertion of the container into an analytic instrument lengthwise so that the barcode reader can be positioned in a space-saving manner for reading out the barcode.

Another embodiment of the container further comprises a seal portion (14) as an additional means for the avoidance of evaporation and thus, cross-contamination and for sealing the cup portion closed by the cap portion during processing and thermal cycling processes. The seal portion may be applied onto the inner side of the cap portion facing the cup portion or may be applied onto the cup portion around the upper opening facing the cap portion.

In particular embodiments of the invention the design of the seal portion (14) of the container may exhibit different cross sectional shapes as depicted in FIG. 7 A-D. The cross sectional shape of the sealing portion is important to form a gas-tight seal. An optimal design of the cross sectional shape of the sealing portion is achieved, when the deformation of the sealing portion caused by the cap portion results in pressure-tight sealing, which means, that the tightness enhances with increasing inner pressure. Thus, as can be seen in FIG. 7A the cross section of the seal portion may be shaped as a rectangle with a chamfered outer edge leading to a deformation of the seal portion mainly to the inner area of the tube. With increasing inner pressure the deformed seal portion is being pressed against the cap even stronger so that a pressure-tight sealing is achieved. Another shape of the seal portion cross section can be seen in FIG. 7B, which does not have a clear tendency to be deformed to the inner area of the tube. However, this shape has a better stress distribution in the seal portion material, which might be an advantage, especially when the cap is kept closed for long periods of time. FIG. 7C shows a shape of the seal portion cross section with the same scope of the shape as shown in FIG. 7A but with a clear geometrical division of the shape into an inner sealing lip to be deformed to the inner area of the tube and a main part which acts as mechanical stop for the cap movement. The shape of the seal portion cross section shown in FIG. 7D is based on the known O-ring geometry, which is typically used as a standard in sealing issues.

Figure 8:
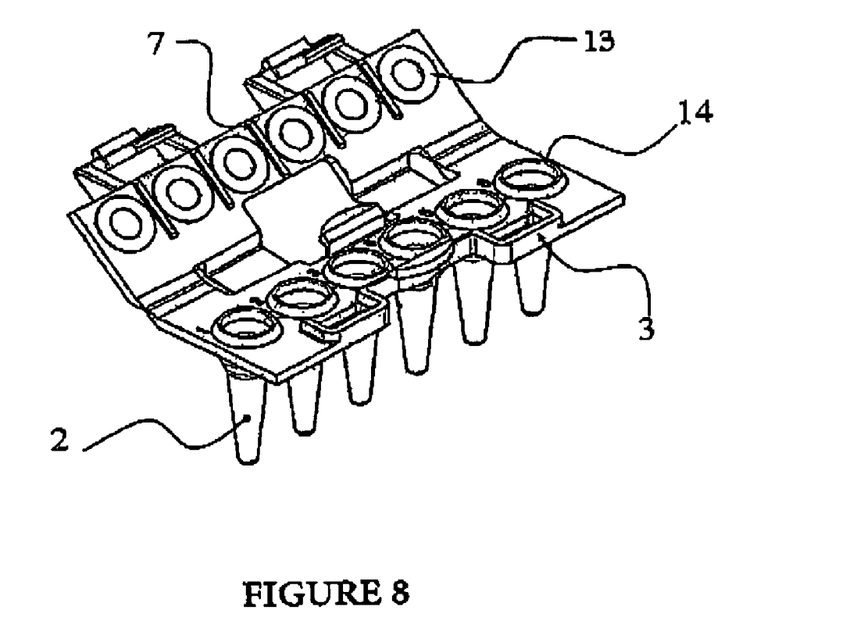
FIG. 8 is a view of a second embodiment of the invention in its open position. The lower side of the cap further comprises a convex or deepened ring area (13) for each cup portion (2).

In a specific embodiment as depicted in FIG. 8 the container on the lower side of its cap portion comprises a convex or deepened ring area (13). The ring area (13) is designed to enable the precise adjustment of possible height differences of the seal portion (14) and/or to compensate a possible warpage of the whole container. Furthermore, it is very difficult to predict the precise movement of the cap portion only by the design of the hinge portions. Therefore, the convex or deepened ring areas are a mechanically simple and effective way of adjusting the actual movement of the cap portion in order to allow the closing of the upper opening of the cup portion by the cap portion even if the cap portion is not precisely located at its predetermined position when the cap portion is tightly fixed to the cup portion in the closed situation. Thus, such an embodiment is advantageous as an additional means to avoid the evaporation of liquid when the container is subjected to heating.

The cup portion of the container of a specific embodiment is made up from a first rigid synthetic material, while the cap portion is made up from a second rigid synthetic material, and the seal portion is made up from a soft synthetic material, wherein the rigid synthetic material is a thermoplastic polymer material and the soft synthetic material is an elastomer polymer material or a thermoplastic elastomer polymer material. In a further embodiment the cup portion, the cap portion, and the seal portion are integral elements of the container and are intractably connected.

In a further embodiment of the container the cup portion of the container comprises tubes having a substantially conical first wall portion and a substantially cylindrical downwards tapered second wall portion, wherein the first wall portion has a substantially thinner wall than the second wall portion and wherein the angle defined by the longitudinal axis through the substantially conically shaped first wall portion may be between 7° and 15°, between 8° and 12°, or between 9° and 11°. Furthermore, the thickness of the first wall portion may be between 0.15 mm and 0.30 mm. In a further embodiment of such containers, the angle defined by the longitudinal axis through the substantially conically shaped first wall portion is about 10° and the thickness of the first wall portion is about 0.2 mm.

Figure 5:
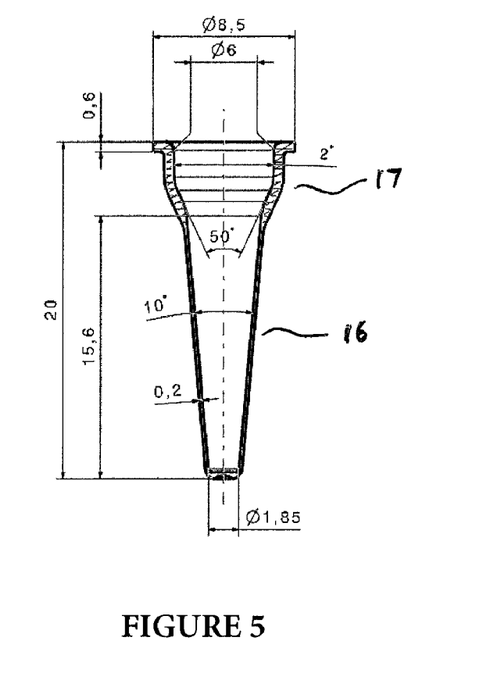
FIG. 5 shows a tube according to a second embodiment of the invention having a first wall portion (16) and a second wall portion (17).

A tube according to the invention as depicted in FIG. 5 has an upper opening and consists of a substantially conical first wall portion and a substantially cylindrical downwards tapered second wall portion, wherein the first wall portion has a substantially thinner wall than the second wall portion and wherein the angle defined by the longitudinal axis through the substantially conically shaped first wall portion may be between 7° and 15°, between 8° and 12°, or between 9° and 11°. Furthermore, the thickness of the first wall portion may be between 0.15 mm and 0.30 mm.

In one embodiment of the tube, the angle defined by the longitudinal axis through the substantially conically shaped first wall portion is about 10° and the thickness of the first wall portion is between 0.15 mm and 0.30 mm, preferably about 0.2 mm.

In another embodiment the tube further comprises a cap portion that is permanently attached to one side of the cup and comprises a cover capable of closing the upper opening of the cup. Preferably the cap portion is permanently attached to one side of the cup via a bistable hinge and is non-transparent.

An advantage of the container and the tube according to certain embodiments of the invention is that the angle defined by the longitudinal ar through the cup portion is between 7° and 15°, leading to a better heat transfer from the heating/cooling block to the fluid and increased temperature homogeneity of the fluid and that the thickness of a first wall portion within the cup portion exhibits a thickness between 0.15 mm and 0.30 mm also leading to a better heat transfer from the heating/cooling block to the fluid and furthermore, to improved transparency characteristics advantageous for the detection measurement.

In another embodiment of the tube, the rte has a cap portion that is permanently attached to one side of the cup portion comprising a cover capable of closing the upper opening of the cup portion. The cap portion may be permanently attached to one side of the cup portion via a bistable hinge. These embodiments are advantageous as they can automatically be processed by an analytical instrument. In a specific embodiment of the invention the cap portion of the tube is non-transparent leading to the advantage of a reduction in autofluorescence and in light scattering as well as an improved recognition of the container when the container surpasses a light barrier.

Figure 6A:
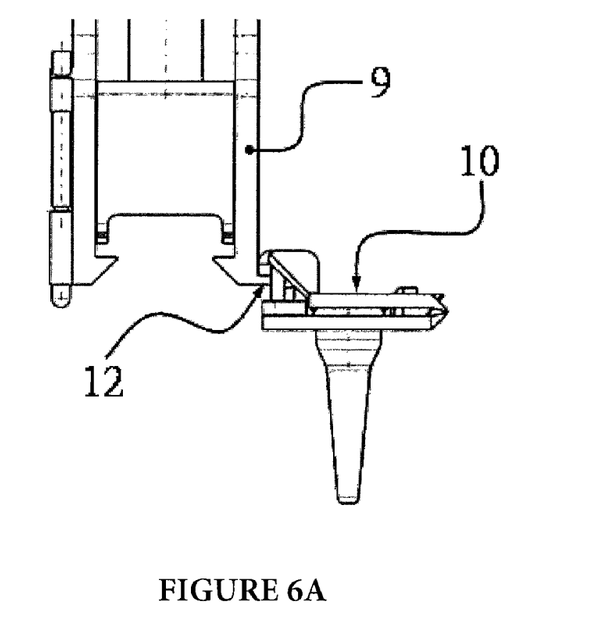
FIG. 6 illustrates the opening (A) and the closing process (B) of a first embodiment of the invention with a handling head (9) comprising a spike (12).

The method for the automated handling of a liquid in an analytical instrument is displayed in FIG. 6. The automated opening of the container in the closed position (10) is shown in FIG. 6A. The handling head (9) approaches the container to the side, where the container exhibits a closure by which the cover of the container is vertically and reversibly fixed to the cup portion. Subsequently, the handling head (9), which in certain embodiments may comprise a spike, horizontally asserts pressure on the closure to release the cover from the vertical and reversible fixation, and may optionally raise the cover by raising the handling head to open the cup portion.

Figure 6B:
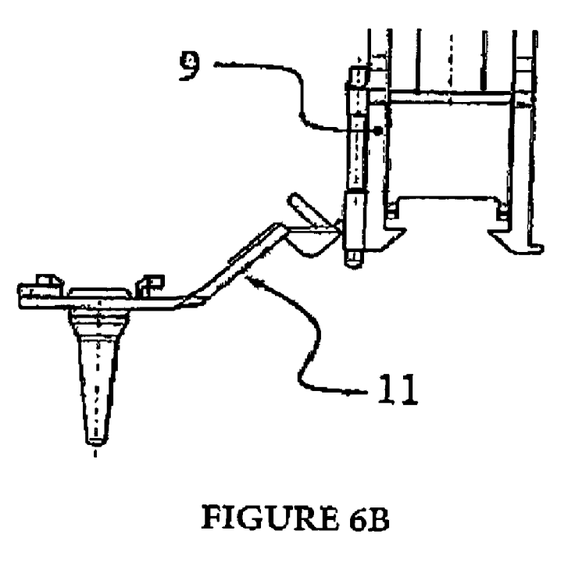
Figure 7A:
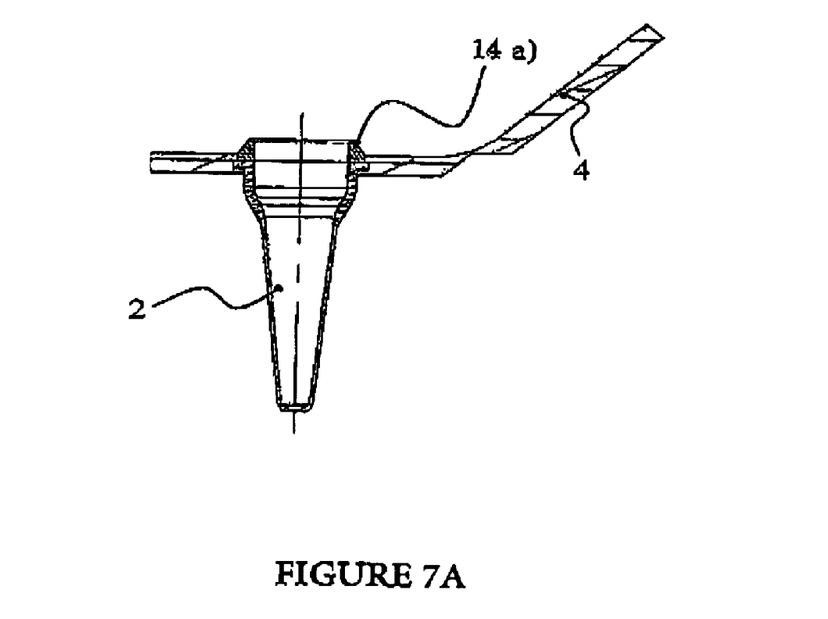
Figure 7B:
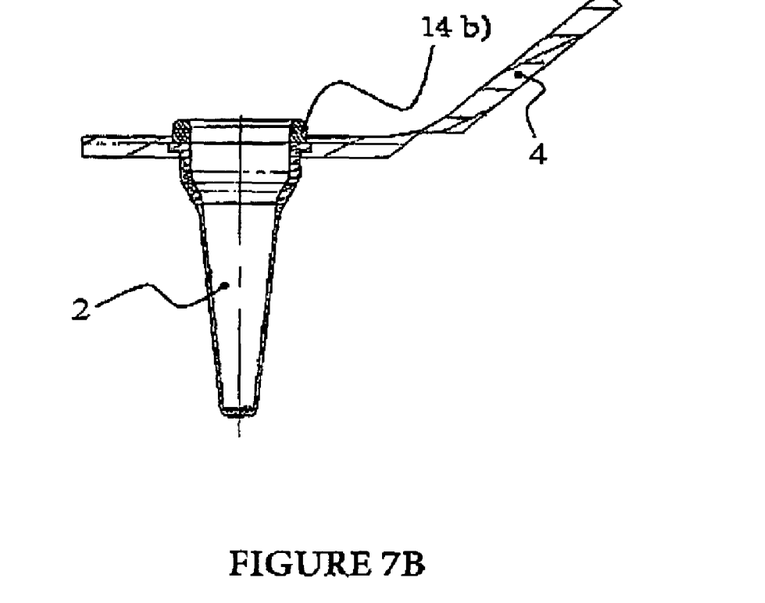
Figure 7C:
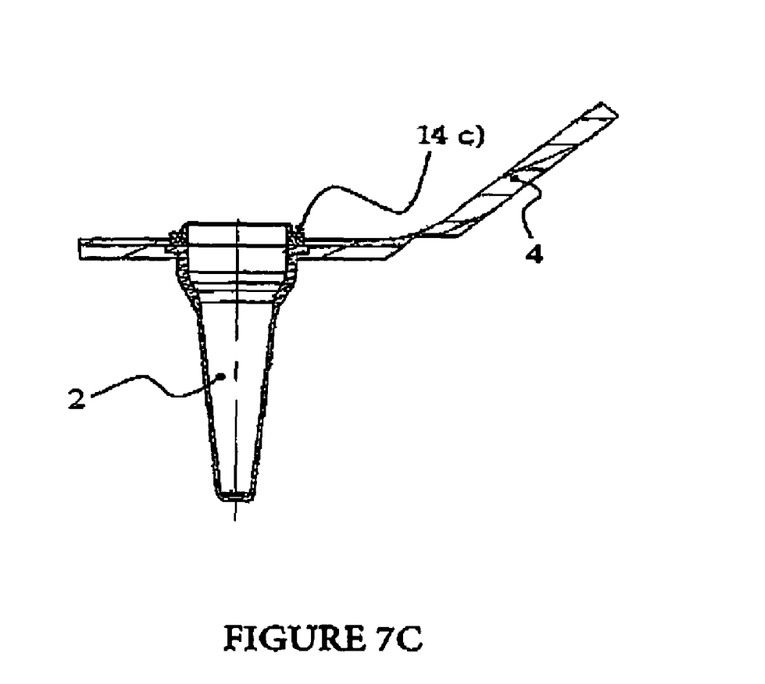
Figure 7D:
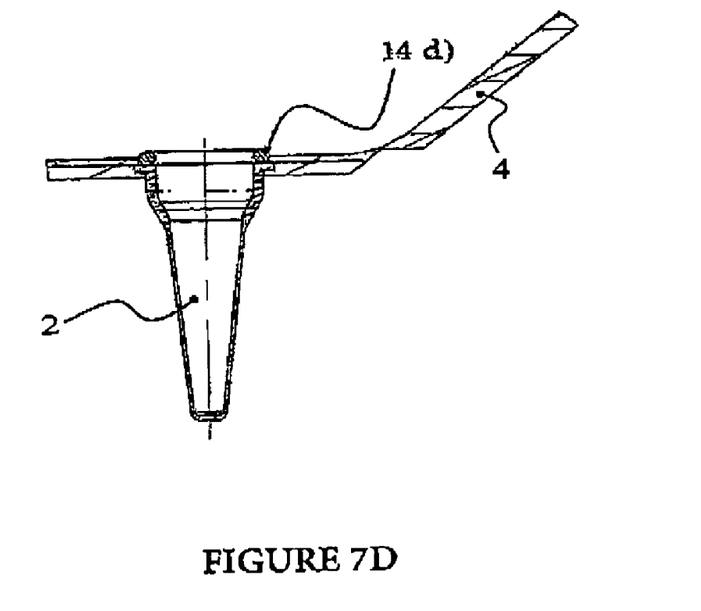

The closing of a container in the open position (11) is shown in FIG. 6B. Here, the handling head (9) approaches the container to the side where the latch-fit from the closure of the opened cover is pointing to. Subsequently, the handling head (9) horizontally moves directly above the container thereby pushing the cover above the upper opening of the cup portion and bringing the snap-latches of the cover in proximity to the latch-fit of the cup portion. In a second vertical move the handling head now asserts pressure on the cover to enable the engagement of the snap-latches into the latch-fits.

In a specific embodiment of the method the handling head further comprises a gripper in order to pick up and transport the container from one position, e.g. the receptacle, within the analytical instrument to another.

In a specific embodiment of the method according to the invention the cup portion of the container is reversibly held down to the receptacle by a movable down holding clamp, while the handling head approaches and operates on the container. This embodiment has the advantage that the container is fired to the receptacle during the operation of the handling head, avoiding the spill of fluid while the cap portion of the container is not firmly fixed to the cup portion of the container and thus, reducing a source for cross-contamination of the reaction mixtures.

Another embodiment of the invention is an instrument for automated handling of a liquid that encompasses a handling head comprising a portion having a spike pointing in horizontal direction (see (12) in FIG. 6) and a portion for vertically picking up items, which in certain embodiments may be pipette tips or containers according to the invention. More preferably the instrument further comprises a control unit to direct horizontal and vertical movement of the handling head.

Vessels for the use in the method or the instrument of the invention may be manufactured wing a production method also provided in the invention. This production method, the so-called multi component injection molding technology, allows the production of the vessels using different materials in one mold. In a first step a first component is injected into the first cavity of the multi component mold. Instead of ejecting this component after opening the mold as done in conventional injection molding the first component remains in one side of the first cavity either in the injection side or in the movable side of the mold. Subsequently, either the injection side or the movable side of the mold is rotated around the injection axis (e.g. an angle of 120° for three components) so that the first cavity with the first component still fixed in faces the second cavity of the other side of the mold. In a second step a second component is filled into the second cavity. In doing so a permanent junction between the first and the second component is obtained when appropriate materials are processed. During this second step the first cavity is filled with the first component for the second time. Hence, either the injection side or the movable side of the mold is rotated around the injection axis (e.g. angle of 120° for three components) for the second time so that the first cavity with the first component still fixed in faces the second cavity and the second cavity with the first and the second component faces the third cavity of the other side of the mold. In a third step a third component is injected. Thus, after three steps the first three-component vessel is completed. Therefore, in each three-step cycle one complete three-component part is produced. In summary, such a production method for a vessel, wherein the vessel is made up of three plastic materials and produced in one mold comprises;

injecting a first component into a first cavity of the multi component mold, rotating the mold around the injection as with the first component remaining in the first cavity and after rotating the mold facing a second cavity, injecting a second component into the second cavity forming a permanent junction between the first and the second component, rotating the mold around the injection axis with the first component remaining in the first cavity and after rotating the mold facing a third cavity, and injecting a third component into the third cavity permanently connecting the third component to the component consisting of the first and the second component.

In a specific embodiment of the invention the vessel manufactured by the production method is the container of the invention. In another specific embodiment of the invention where the vessel is the container of the invention the container contains a seal portion located between the cup portion and the cap portion when the container is in the locked position.

A vessel manufactured according to the production method comprises a cup portion molded from a first rigid synthetic material, a cap portion molded from a second rigid synthetic material, and a seal portion molded from a soft synthetic material, wherein the rigid synthetic material is a thermoplastic polymer material and the soft synthetic material is an elastomer polymer material or a thermoplastic elastomer polymer material. Furthermore, the cup portion, the cap portion, and the seal portion are integral elements of the vessel and are intractably connected. Disassembly of the three integral elements would lead to a destruction of the vessel. Alternatively, the vessel may also be assembled after manufacturing the single materials by conventional injection molding.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A container for automated handling a liquid on an analytical instrument, comprising:
   a cup portion comprising one or more tubes having an upper opening and further comprising one or more latch-fits located at the side of the cup portion,
   a cap portion permanently attached to one side of the cup portion comprising a cover closing the upper opening and further comprising one or more snap-latches located in a manner to reversibly engage into the latch-fit of the cup portion.
   wherein the snap-latch of the cap portion is held by the latch-fit of the cup portion to form a closure so that the cover is vertically and reversibly closing the opening, and
   wherein the snap-latch comprises a sloped plain accessible by a handling head from the side of the cup portion to allow releasing the cap portion from the cup portion by horizontally asserting pressure to the plain.

2. The container according to claim 1, wherein the cover of the cap portion comprises at least one partition bar positioned in such a way to separate one upper opening of a cup portion from a second adjacent upper opening when the cover of the cap portion is tightly fixed to the cup portion.

3. The container according to claim 1, wherein the cap portion is reversibly attached to the cup portion via a spring lock consisting of the latch-fit and the snap-latch.

4. The container according to claim 1, wherein the cap portion is permanently attached to one side of the cup portion via a bistable hinge.

5. The container according to claim 1, wherein the cap portion is non-transparent.

6. The container according to claim 1, wherein the external part of the cap portion comprises a barcode, the barcode being divided into four parts and wherein the four parts of the barcode assemble one full length barcode.

7. The container according to claim 1, wherein the container additionally contains a seal portion located between the cup portion and the cap portion, when the cover of the cap portion is tightly fixed to the cup portion.

8. The container according to claim 7, wherein the cup portion is made up from a first rigid synthetic material, the cap portion comprising the cover closing is made up from a second rigid synthetic material, and the seal portion is made up from a soft synthetic material.

9. The container according to claim 7, wherein the seal portion is applied onto the cup portion around the upper opening facing the cap portion.

10. The container according to claim 1, wherein the tube of the cup portion consists of a substantially conical first wall portion and a substantially cylindrical downwards tapered second wall portion, wherein the first wall portion has a substantially thinner wall than the second wall portion and wherein the angle defined by a longitudinal axis that travels through the center of the tube and the substantially conically shaped first wall portion is between 7° and 15°.

11. The container according to claim 10, wherein the angle defined by the longitudinal axis that travels through the center of the tube and the substantially conically shaped first wall portion is about 10°.

12. The container according to claim 10, wherein the thickness of the first wall portion is between 0.15 mm and 0.30 mm.

13. The container according to claim 10, wherein the thickness of the first wall portion is about 0.2 mm.

14. The container according to claim 1, wherein the container consists of an alignment of 2 to 12 tubes each having an opening, wherein all openings can be closed and opened by the cover of the cap portion simultaneously and automatically.

* * * * *